United States Patent
Estes et al.

(10) Patent No.: US 6,209,886 B1
(45) Date of Patent: Apr. 3, 2001

(54) RESECTING TOOL WITH INDEPENDENT VARIABLE AXIAL EXTENSION FOR TOOL IMPLEMENTS AND GUIDE SLEEVES

(75) Inventors: Larry Dale Estes, N. Richland Hills; Ray E. Umber; Gary B. Gage, both of Arlington, all of TX (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/303,474

(22) Filed: Apr. 30, 1999

(51) Int. Cl.$^7$ .............................. B23B 31/20; A61B 17/32
(52) U.S. Cl. .............................. 279/50; 279/52; 279/143; 408/239 A; 433/129; 606/170; 606/180
(58) Field of Search ....................... 279/50–52, 143–145; 433/127–129; 606/79, 80, 170, 180; 408/239 R, 239 A, 240; 409/181, 182

(56) References Cited

U.S. PATENT DOCUMENTS

| | | |
|---|---|---|
| 2,465,837 | 3/1949 | Benjamin et al. . |
| 3,035,845 | 5/1962 | Benjamin . |
| 3,332,693 | 7/1967 | Armstrong et al. . |
| 3,400,459 | 9/1968 | Stemler . |
| 3,488,850 | 1/1970 | Lieb et al. . |
| 3,631,597 * | 1/1972 | Lieb et al. ............................ 433/129 |
| 3,727,928 | 4/1973 | Benjamin . |
| 4,114,276 * | 9/1978 | Malata et al. ......................... 433/129 |
| 4,167,062 * | 9/1979 | Page, Jr. et al. ..................... 433/129 |
| 4,202,644 | 5/1980 | Soussloff . |
| 4,387,906 | 6/1983 | Nicolin . |
| 4,582,332 | 4/1986 | Sekino et al. . |
| 4,725,064 | 2/1988 | Glimpel et al. . |
| 4,817,972 | 4/1989 | Kubo . |
| 5,265,343 | 11/1993 | Pascaloff . |
| 5,380,333 | 1/1995 | Meloul et al. . |
| 5,402,580 | 4/1995 | Seto et al. . |
| 5,439,005 | 8/1995 | Vaughn . |
| 5,478,093 | 12/1995 | Eibl et al. . |
| 5,505,737 | 4/1996 | Gosselin et al. . |
| 5,569,256 | 10/1996 | Vaughen et al. . |
| 5,584,689 * | 12/1996 | Loge .................................... 433/128 |
| 5,741,263 | 4/1998 | Umber et al. . |
| 5,823,774 * | 10/1998 | Abbott et al. ......................... 606/180 |
| 6,000,940 * | 12/1999 | Buss et al. ........................... 433/127 |

* cited by examiner

*Primary Examiner*—Steven C. Bishop
(74) *Attorney, Agent, or Firm*—James E. Bradley; Shawn Hunter; Felsman, Bradley, Vaden, Gunter & Dillon (57) ABSTRACT

A resecting tool contains a rotatable chuck inside a base for engaging the drive shaft of a motor. The chuck extends into a tubular casing that has an outer actuator sleeve. The sleeve is limited to rotation relative to the casing and is used to move a pair of locking elements or balls in separate helical slots in the casing. Each ball is seated in a collar that abuts a collet receiver inside the casing. During implement changeover, the collar abuts the collet receiver and acts as a brake to prevent accidental actuation of the chuck of the tool. The collet receiver is spring-biased into contact with a first collet which closely receives a tool implement within the resecting tool. The sleeve is used to manipulate the collet to clamp onto and unclamp the tool implement. A collet coupling is located on the front end of the casing and has a collet nut on its forward end. The collet nut houses a second collet with a serpentine cut for engaging and retaining a guide sleeve for supporting the tool implement. Both collets are designed to engage and lock onto tool implements and guide sleeves at variable distances along their axial lengths.

36 Claims, 5 Drawing Sheets

RESECTING TOOL WITH INDEPENDENT VARIABLE AXIAL EXTENSION FOR TOOL IMPLEMENTS AND GUIDE SLEEVES

TECHNICAL FIELD

This invention relates in general to surgical resecting tools for cutting human bone and in particular to a resecting tool which is capable of a range of independent extension lengths for both the tool implement and its guide sleeve.

BACKGROUND ART

A surgical resecting tool for cutting human bone uses a detachable motor coupled to the end of a hose to drive a chuck located inside the tool. The chuck engages the shaft of a tool implement which extends from the resecting tool. The distal end of the implement has a tool head which may be configured to perform a variety of procedures. A guide sleeve is used in conjunction with the implement to further support the otherwise cantilevered implement. The guide sleeve also extends from the resecting tool and is concentric with the implement. The motor rotates the chuck to drive the implement at very high rotational speeds within the guide sleeve.

In one type of prior art, the chuck was tightened by a threaded nut to frictionally grip the shaft for transmitting torque. In another type of prior art tool, the shaft of the implement has an axial grip feature and a drive feature, such as a flat, that interfaces with and is closely received by a drive key on the chuck inside the resecting tool. These grip and drive features require precise tolerances and axial positioning within the tool when the implement is installed.

In some tools, the guide sleeve can be adjusted relative to the resecting implement to vary the axial distance that the guide sleeve extends from the tool. Also, quick-release features are known. Still, improvements to these prior art tools are desired.

SUMMARY OF THE INVENTION

A resecting tool contains a rotatable chuck inside a base for engaging the drive shaft of a motor. The chuck extends into a tubular casing that has an outer actuator sleeve. The sleeve is limited to rotation relative to the casing and is used to move a pair of locking elements or balls in separate helical slots in the casing. Each ball is seated in a collar that abuts a collet receiver inside the casing. During implement changeover, the collar abuts the collet receiver and acts as a brake to prevent accidental actuation of the chuck and the tool implement. The collet receiver is spring-biased into contact with a first collet which closely receives a tool implement within the resecting tool. The sleeve is used to manipulate the collet to clamp onto and unclamp the tool implement.

A collet coupling is located on the front end of the casing and has a collet nut on its forward end. The collet nut houses a second collet with a serpentine cut for engaging and retaining a guide sleeve for supporting the tool implement. Both collets are designed to engage and lock onto tool implements and guide sleeves at variable distances along their axial lengths.

BRIEF DESCRIPTION OF THE DRAWINGS

So that the manner in which the features, advantages and objects of the invention, as well as others which will become apparent, are attained and can be understood in more detail, more particular description of the invention briefly summarized above may be had by reference to the embodiment thereof which is illustrated in the appended drawings, which drawings form a part of this specification. It is to be noted, however, that the drawings illustrate only a preferred embodiment of the invention and is therefore not be considered limiting of its scope as the invention may admit to other equally effective embodiments.

MODE FOR CARRYING OUT THE INVENTION

Figure 1A:
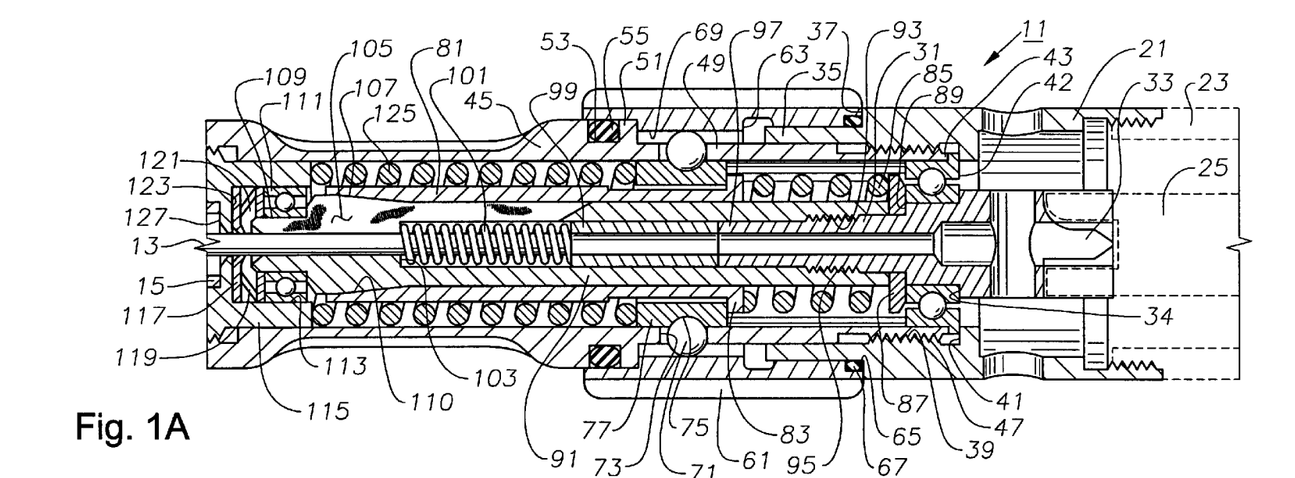
FIG. 1A is a sectional side view of a rearward portion of a resecting tool with a fully inserted tool implement and guide sleeve, wherein the resecting tool is constructed in accordance with the invention.
Figure 1B:
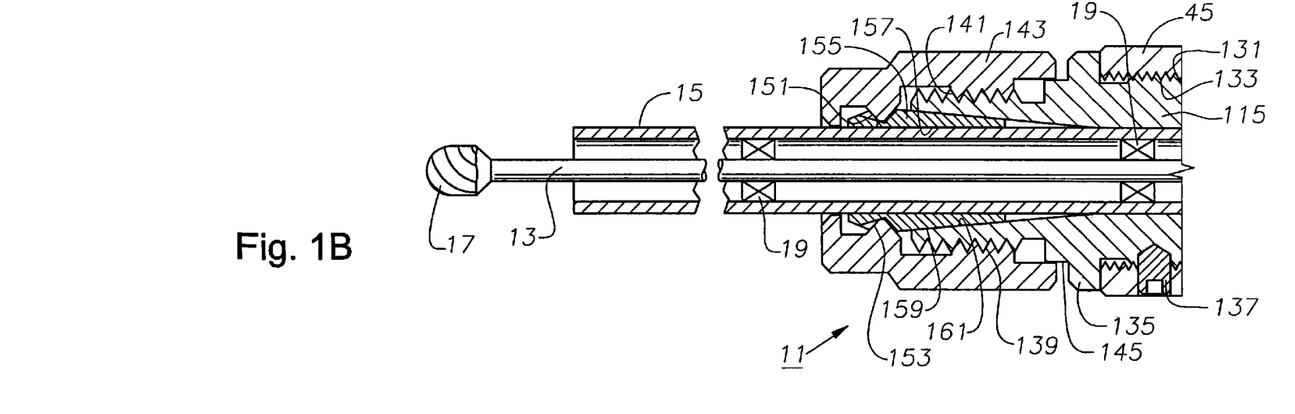
FIG. 1B is a sectional side view of a forward portion of the tool of FIG. 1A.

Referring to FIGS. 1A and 1B, a resecting tool 11 for manipulating a tool implement 13 and guide tube or sleeve 15 is shown. Tool implement 13 has an elongated, thin cylindrical shaft with a tool head 17 on its forward end. Although only one embodiment is shown, tool head 17 may comprise many different forms, depending upon the procedure being performed by the user. Guide sleeve 15 is a thin-walled, cylindrical member which supports the shaft of implement 13 with multiple bearings 19. Both implement 13 and guide sleeve 15 have smooth exteriors which are closely received within tool 11. In FIGS. 1A and 1B, implement 13 and guide sleeve 15 are inserted to a maximum depth within tool 11, as will be described in detail below.

Figure 3A:
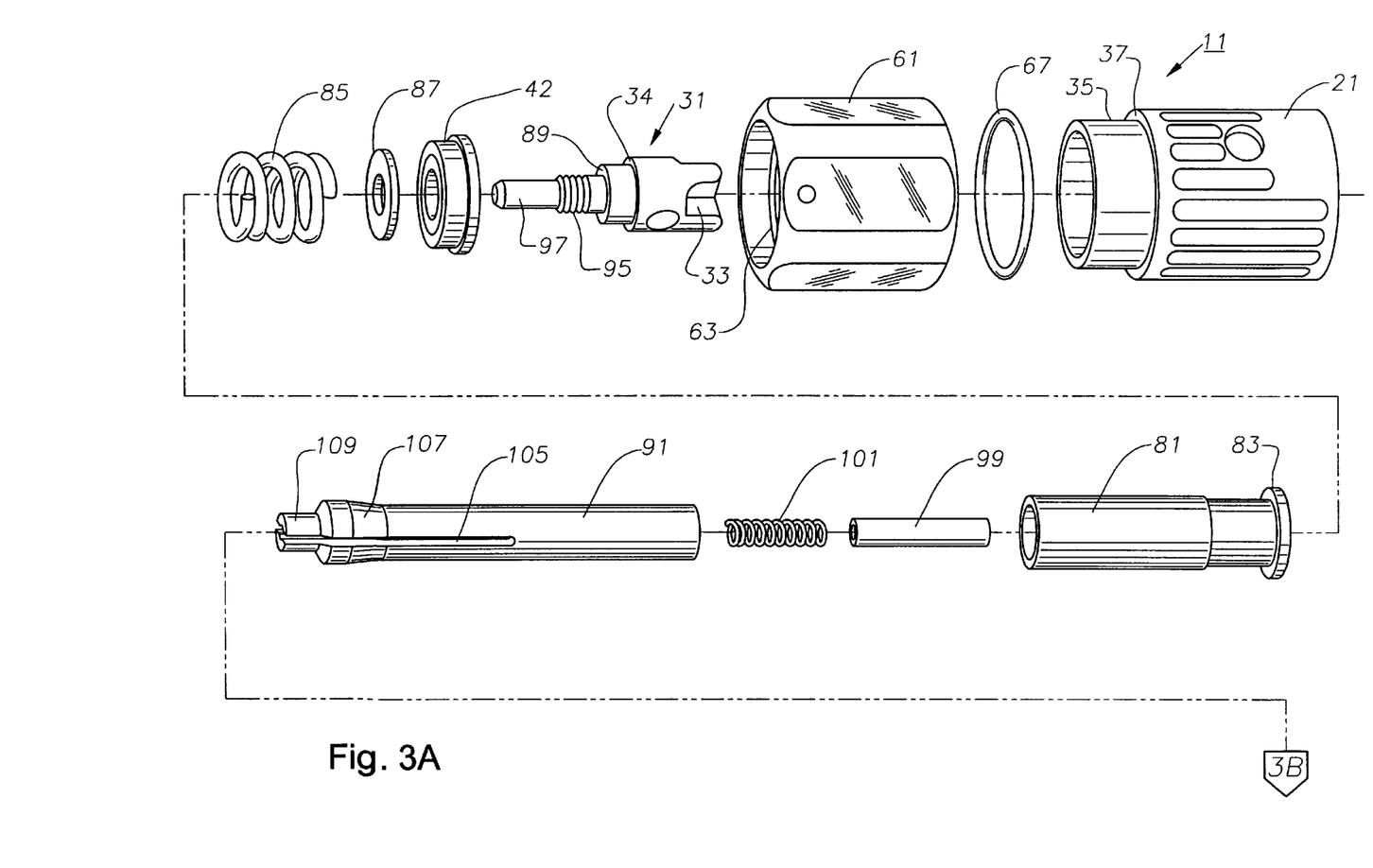
FIG. 3A is an exploded, isometric view of the rearward portion of the tool of FIG. 1A without the tool implement or guide sleeve.

As shown in FIGS. 1A and 3A, the rearward end of tool 11 has a cylindrical base 21 with internal threads that attach to a motor 23. Motor 23 has a concentric drive shaft 25 that engages a chuck or drive coupling 31 located inside base 21. Coupling 31 has drive members 33 for engaging drive shaft 25, and a shoulder 34 near its midsection. The forward end of base 21 has a concentric hub 35 with a reduced diameter which defines a shoulder 37 therebetween.

Base 21 also contains internal threads 39 and an internal flange 41 located rearward of threads 39 (FIG. 1A). The rearward end 43 of an elongated, generally tubular casing 45 (FIG. 3A) captures a roller bearing 42 against coupling 31. Bearing 42 has a lip on its outer race which is engaged by end 43 against flange 41 to prevent the axial movement of bearing 42. The inner race of bearing 42 rests against an outer surface of coupling 31 and its shoulder 34. Casing 45 has external threads 47 for engaging threads 39 on base 21. End 43 and threads 47 are located on an elongated hub 49 which protrudes rearward from casing 45. Hub 49 has a central flange 51 which defines a recess 53 on its forward side for containing an O-ring 55.

A large diameter actuator sleeve 61 surrounds hubs 35, 49 and has an annular boss 63 on its interior surface (FIGS. 1A and 3A). The inner surface of boss 63 smoothly engages the outer surface of hub 49. The forward end of boss 63 abuts flange 51 on hub 49 (FIG. 3B), and the rearward end of sleeve 61 abuts shoulder 37 (FIG. 3A) to prevent the axial movement of sleeve 61. Sleeve 61 has an annular notch 65 on its inner rearward end for capturing an O-ring 67 against shoulder 37 and hub 35. The rearward end of the inner surface of sleeve 61 is smooth and closely receives the outer surface of hub 35 for smooth rotation of sleeve 61 relative to casing 45. The forward end of the inner surface of sleeve 61 is also smooth and closely receives the outer diameter of casing 45 and flange 51 to capture O-ring 55 in recess 53. Boss 63 also has a pair of axial grooves 69 which are located 180 degrees apart from each other. Each groove 69 closely receives the upper end of a locking element or actuator ball 71.

Figure 3B:
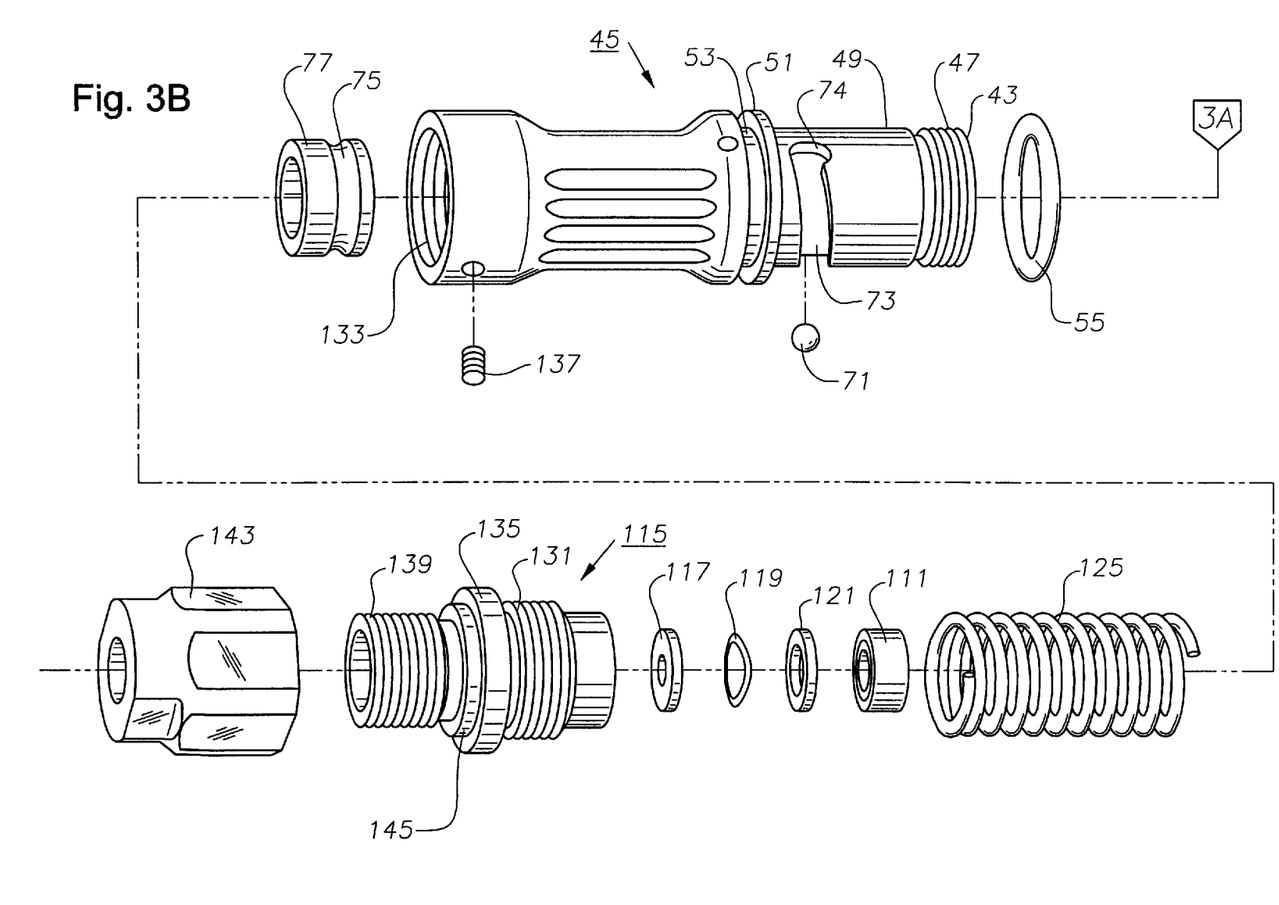
FIG. 3B is an exploded, isometric view of the forward portion of the tool of FIG. 1B without the tool implement or guide sleeve.

Referring to FIGS. 1A and 3B, each ball 71 is movably mounted in its own helical slot 73 in hub 49 of casing 45. Slots 73 have an axial dimension or width which is slightly greater than the diameter of balls 71. Each slot 73 has a circumferential length of approximately 120 degrees. A locking circular detent 74 (one shown) is located on each end of each slot 73 for capturing balls 71. Slots 73 extend completely through hub 49 to expose balls 71 to the interior of casing 45. The lower end of each ball 71 is seated in a concave recess 75 in a hollow collar 77. Thus, the radial distance from the bottom of recess 75 to the top of each groove 69 is slightly greater than the diameter of balls 71. Collar 77 is located within casing 45 and has an outer diameter that is closely received by the inner diameter of hub 49. Rotating sleeve 61 causes balls 71 to move along helical slots 73, which in turn moves collar 77 forward or rearward.

As shown in FIGS. 1A and 3A, an elongated, cylindrical tool collet receiver 81 is located radially inward of but does not touch casing 45. Collet receiver 81 is hollow and has an external flange 83 on its rearward end. The forward side of flange 83 engages the rearward end of collar 77. The rearward side of flange 83 abuts the forward end of a rearward compression spring 85. The rearward end of spring 85 abuts a spacer 87, which itself abuts the inner race of bearing 42 and a shoulder 89 on coupling 31.

Spring 85 surrounds the rearward end of an elongated, generally cylindrical tool implement collet 91 which also abuts spacer 87. Collet 91 is hollow and has internal threads 93 near its rearward end for engaging a set of external threads 95 on coupling 31. The shaft 97 of coupling 31 is closely received within collet 91. The forward end of shaft 97 abuts the rearward end of a tubular spacer 99 which is also closely received by the interior of collet 91. The forward end of spacer 99 acts as a backstop for the maximum insertion depth of tool implement 13 and the rearward end of an inner compression spring 101. The forward end of spring 101 abuts a shoulder 103 in collet 91 to maintain spacer 99 in position. Spring 101 serves only as a positioner for spacer 99 and essentially does not compress or expand during operation.

The front end of collet 91 is split with axial grooves 105 for adjustably engaging the shaft of tool implement 13. Thus, collet 91 will contract and expand radially to frictionally engage and release, respectively, implement 13. Collet 91 also has an external taper 107 which transitions into a relatively small diameter neck 109 on the front end of collet 91. Taper 107 slidingly engages a taper 110 on the inner surface of the front end of collet receiver 81. The inner race of a forward roller bearing 111 radially supports neck 109 (FIGS. 1A and 3B). The outer race of bearing 111 is captured in an axial hole 113 in a collet coupling 115. From front to back, a seal 117, curved disc spring 119, and shim 121 are located between a shoulder 123 in hole 113 and the front side of bearing 111. The rearward end of collet coupling 115 abuts the forward end of a large compression spring 125. The rearward end of spring 125 abuts the forward end of collar 77. Spring 125 is located inside casing 45 and it surrounds a substantial portion of the axial length of collet receiver 81. Springs 125 and 85 (described above) provide counterbalancing axial forces against collar 77 and flange 83. Note that in the fully inserted position, guide sleeve 15 abuts a shoulder 127 located inside collet coupling 115 (left edge of FIG. 1A). When collar 77 moves rearward due to rotation of sleeve 61 and balls 71, collet receiver 81 moves rearwared, allowing the front end of collet 91 to expand and release implement 13.

Referring now to FIGS. 1B and 3B, collet coupling 115 has a set of external threads 131 on its rearward end for engaging internal threads 133 on the forward end of casing 45. The front rim of casing 45 abuts the rear surface of an external flange 135 on collet coupling 115. A radial set screw 137 locks collet coupling 115 to casing 45. Collet coupling 115 also has external threads 139 on its forward end for engaging the internal threads 141 of a collet nut 143. The inner surface on the rearward end of collet nut 143 closely receives a hub 145 on collet coupling 115. Collet nut 143 also contains a pointed, inner annular rib 151 near its front end. Rib 151 is conical in profile and is provided for engaging an external, annular groove 153 in a guide sleeve collet 155 (FIG. 1B). Rib 151 releasably engages groove 153 so that collet 155 may be readily snapped into and out of collet nut 143 for easy cleaning.

Figure 4:
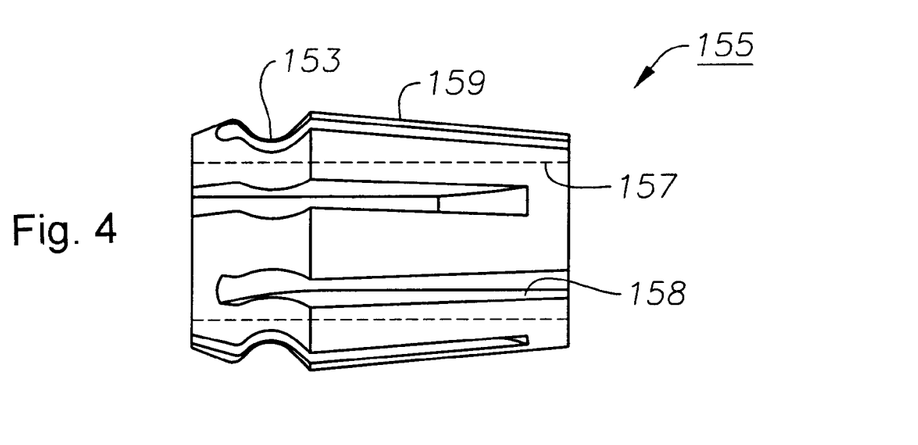
FIG. 4 is a side view of a serpentine collet for the guide sleeve.
Figure 5:
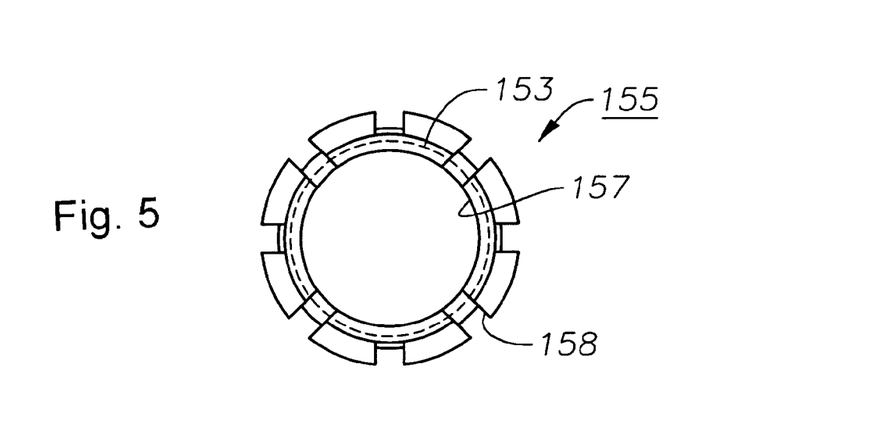
FIG. 5 is a rear axial view of the collet of FIG. 4.

As shown in FIGS. 4 and 5, collet 155 has a cylindrical bore 157 and a serpentine cut 158 that allows it to adapt to and closely receive guide sleeves 15 of various sizes. The shape of cut 158 increases the contact area between collet 155 and guide sleeve 15 to provide superior grip therebetween. When collet nut 143 is moved, collet 155 will contract or expand radially to frictionally engage and release, respectively, guide sleeve 15. The exterior of collet 155 has an axial taper 159 and decreases in diameter from front to back such that it is closely received by the tapered bore 161 at the front end of collet coupling 115. Like taper 159, the inner diameter of bore 161 decreases from front to back. Tightening collet nut 143 causes collet 155 to contract radially.

Prior to the installation of tool implement 13 and guide sleeve 15, each collet 91, 155 of resecting tool 11 must be set to its disengaged or unlocked position. Guide sleeve collet 155 is prepared to receive guide sleeve 15 by rotating collet nut 143 to move axially toward flange 135 on collet coupling 115. This motion causes the tapered surfaces 159, 161 of collet 155 and collet coupling 115, respectively, to slightly increase in diameter due to the spring-like properties of the serpentine cut in collet 155.

Figure 2A:
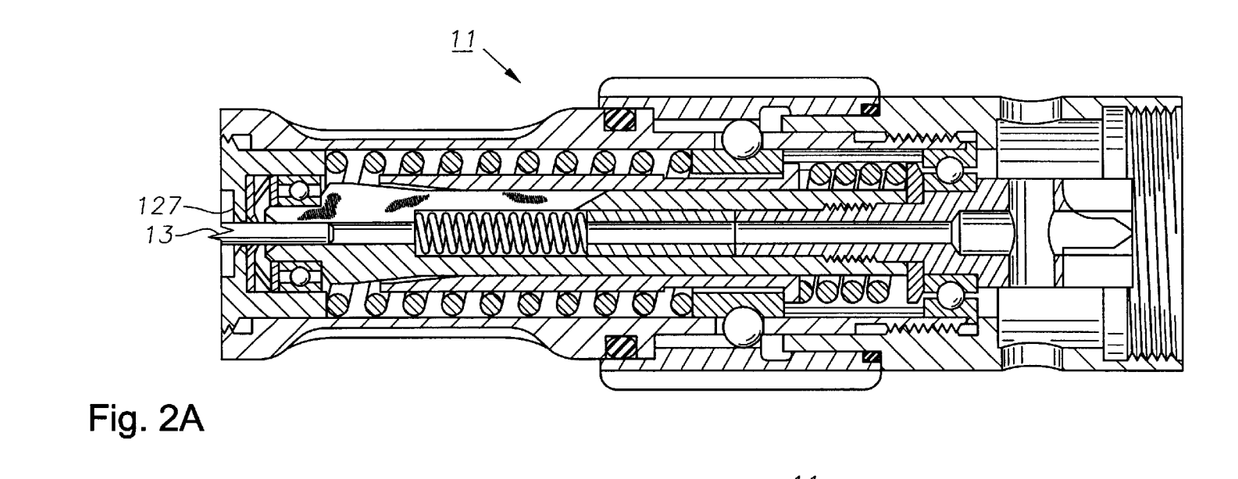
FIG. 2A is a sectional side view of the rearward portion of the tool of FIG. 1A with the tool implement and guide sleeve at a minimum insertion distance.
Figure 2B:
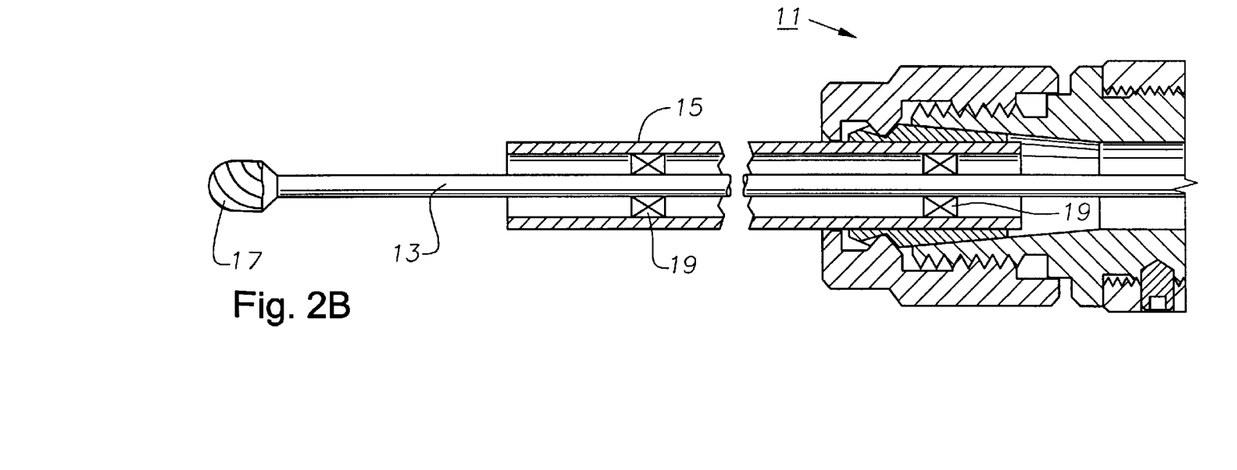
FIG. 2B is a sectional side view of the forward portion of the tool of FIG. 1B with each of the tool implement and guide sleeve at a minimum insertion distance.

With collet 155 in this position, guide sleeve 15 may be inserted into the hole on the front end of collet nut 143 to any depth from the minimum depth depicted in FIG. 2B (this is also the maximum axial extension of sleeve 15 out of tool 11), to the maximum depth depicted in FIGS. 1A and 1B (the minimum axial extension of sleeve 15), depending upon the procedure being performed by the user. Thus, the axial extension of guide sleeve 15 may be varied by approximately one to two inches. At the minimum depth, the rearward end of guide sleeve 15 is substantially radially aligned with the rearward end of collet 155. This position assures full surface area contact between the inner surface of collet 155 and guide sleeve 15. At the maximum depth, the rearward end of guide sleeve 15 abuts shoulder 127 in collet coupling 115. At either depth, the surface area of contact between collet 155 and guide sleeve 15 is the same.

When guide sleeve 15 is at the desired depth, collet nut 143 is rotated in the opposite direction (away from flange 135 of collet coupling 115) until guide sleeve 15 is tightly clamped inside tool 11. By moving collet nut 43 to its locked position, the internal taper 161 in collet coupling 115 presses on the external taper 159 on collet 155, thereby overcoming its spring-like resilience to clamp it down on guide sleeve 15. The rib 151 inside collet nut 143 stays seated in the groove 153 in collet 155 to retain collet 155 in the proper position inside collet nut 143 and collet coupling 115 at all times.

Resecting tool 11 is similarly prepared to receive tool implement 13 by rotating sleeve 61 to its unlocked position (FIG. 2A). Sleeve 61 is limited to rotational motion and it and casing 45 have external markings (not shown) which permit the user to select the desired position. With sleeve 61 in the unlocked position, balls 71 are lodged in the detents 74 on the rearward end of slots 73. Since detents 74 are slightly misaligned with the path defined by slots 73, the user will detect a tactile verification of the visual indication of the markings on sleeve 61 and casing 45. As balls 71 move to this position, they are forced to move radially by the side walls of grooves 69 in sleeve 61. Balls 71 also move in an axially rearward direction in their helical slots 73 until they seat in the rearward detents 74. Thus, the grooves 69 in sleeve 61 also allow for the axial motion of balls 71, and the slots 73 also allow for their radial motion. Casing 45 is stationary at all times. In this unlocked position, spring 125 is expanded and spring 85 is collapsed.

In the unlocked position, collar 77 pushes collet receiver 81 rearward such that its taper 110 disengages taper 107 on collet 91. This motion allows collet 91 to expand and increase its bore diameter for receiving the shaft of tool implement 13. Note that collet 91 is locked from axial movement and is only permitted to rotate with coupling 31 relative to tool 11. However, in the unlocked position, collar 77 acts as a brake against accidental rotation of tool implement 13 since collar 77 abuts flange 83 on collet receiver 81. This safety precaution during implement installation and/or removal is a significant improvement over prior art resecting tools.

Like guide sleeve 15, tool implement 13 may be inserted to any depth between the minimum depth depicted in FIG. 2A (also its maximum axial extension from tool 11), to the maximum depth depicted in FIG. 1A (its minimum axial extension), depending upon the procedure being performed by the user. Thus, the axial extension of tool implement 13 may be varied by approximately one to two inches. At the minimum insertion depth, the rearward end of tool implement 13 is substantially radially aligned with the rearward end of the neck 109, which provides the primary surface gripping area for securing tool implement 13 from slipping relative to collet 91. At the maximum insertion depth, the rearward end of tool implement 13 abuts spacer 99. The shaft of implement 13 is larger in diameter than the bore of spacer 99 and, thus, abuts spacer 99 in the minimum extension position.

After the user positions tool implement 13 at a desired axial extension, sleeve 61 is rotated in the reverse direction to the locked position. With this motion, balls 71 are moved out of rearward detents 74 and translated along slots 73 to the forward detents 74, thereby moving collar 77 forward. This causes spring 125 to collapse and spring 85 to expand to move collet receiver 81 forward. The tapers 107, 110 of collet 91 and collet receiver 81, respectively, interface to squeeze neck 109 around the shaft of tool implement 13 to lock it from axial and rotational movement relative to collet 91. The relative positionings of tool implement 13 and guide sleeve 15 may be repositioned or removed entirely at any time by following the same steps described above.

Tool 11 is now ready for use. With motor 23 attached to base 21, drive shaft 25 will rotate drive coupling 31, collet receiver 81, collet 91 and tool implement 13 to perform resecting procedures. Guide sleeve 15 is stationary and does not rotate.

The invention has several advantages. This resecting tool is compatible with many types of tool implements whether or not they have drive shoulders or other drive features. As described above, the tool is ideally suited for implements with a smooth cylindrical surface. Both the tool implement and the drive sleeve may be axially repositioned to any desired position between the minimum and maximum axial extensions. Moreover, the tool implement and drive sleeve are positioned independently so that optimal spacing relationships may be obtained. The braking feature also prevents accidental actuation of the resecting tool to minimize risk of injury to the user. The serpentine collet provides improved grip on the guide sleeve, is easily removed from the collet nut for cleaning, and allows the guide sleeve to have a significant range of axial extension from the tool.

While the invention has been shown or described in only some of its forms, it should be apparent to those skilled in the art that it is not so limited, but is susceptible to various changes without departing from the scope of the invention. For example, rather than having a rotating sleeve with balls to extend and retract the collet, a sleeve which is manually pushed or pulled to actuate the collet would be feasible.

We claim:

1. A surgical resecting tool for cutting bore that is adapted to be driven by a motor for rotating a tool implement having a shaft and a tool head on one end of the shaft, comprising:

a base having an axis and adapted to be attached to the motor;

a drive chuck located inside the base for axial rotation therein and adapted to be coupled to and rotationally driven by the motor;

an implement actuation mechanism mounted to the base and having an external, manually engageable portion that is moveable between locked and unlocked positions for radially moving an implement collet into and out of frictional engagement, respectively, with the shaft of the implement; and wherein an amount of axial extension of a tool head of the implement from the resecting tool may be selected by a user by axially repositioning the shaft of the implement within an implement collet;

a guide sleeve for closely receiving the tool implement; and a guide sleeve actuation member mounted to a front end of the base and having an external, manually engageable portion, the guide sleeve actuation member being manually moveable relative to the base.

2. The tool of claim 1, further comprising:

a guide sleeve collet located inside the front end of the base and the guide sleeve actuation member, the guide sleeve collet having an open end that is adapted to closely receive the guide sleeve, the guide sleeve collet being radially expansible and contractible in response to movement of the guide sleeve actuation member relative to the base; and wherein an amount of axial extension of the guide sleeve from the resecting tool may be selected by the user, independently of the axial extension of the implement, by axially repositioning the guide sleeve within the guide sleeve collet.

3. The tool of claim 2 wherein the guide sleeve collet has a serpentine cut and an external taper for engaging an internal taper in the guide sleeve actuation member.

4. The tool of claim 2 wherein the guide sleeve actuation mechanism comprises a collet nut that threadingly engages the front end of the base, the collet nut having an internal, circumferentially-extending rib for engaging an annular recess in an exterior of the guide sleeve collet, so that axial movement of the collet nut relative to the base as the collet nut is rotated moves the guide sleeve collet axially.

5. The tool of claim 4 wherein an interior surface of the front end of the base is tapered to couple with a taper on the exterior of the guide sleeve collet, such that axial movement of the guide sleeve collet by the collet nut radially expands and contracts the guide sleeve collet.

6. The tool of claim 1 wherein the implement actuation mechanism comprises:
    a sleeve mounted to an exterior of the base for manual rotation relative thereto between the locked and unlocked positions;
    a collet receiver; and
    a linkage extending between the sleeve and the collet receiver for converting the rotational movement of the sleeve into axial motion of the collet receiver.

7. The tool of claim 6, further comprising a pair of springs located within the base in engagement with the collet receiver in axial opposition to each other for counterbalancing the implement actuation mechanism between the locked and unlocked positions.

8. The tool of claim 6 wherein the base has a helical slot and the linkage comprises a locking element carried in the helical slot in the base between the sleeve and the collet receiver, wherein rotation of the sleeve translates the locking element from one end of the slot to the other to axially reposition the collet receiver relative to the implement collet.

9. The tool of claim 8 wherein the locking element comprises a ball.

10. The tool of claim 1 wherein the implement actuation mechanism engages the drive chuck to act as a brake against its rotation when in the unlocked position.

11. A surgical resecting tool for cutting bone that is adapted to be driven by a motor for rotating a tool implement having a shaft and a tool head on one end of the shaft, comprising:
    a generally tubular base having a longitudinal axis and adapted to be attached to the motor;
    a drive chuck located inside the base for coaxial rotation relative thereto and adapted to be coupled to and rotationally driven by the motor;
    an implement collet mounted to the chuck and having an axial opening and a tapered exterior, the implement collet being radially expansible and contractible about the opening for closely receiving the shaft of a tool implement;
    a collet receiver having a tapered inner surface that slidingly engages the tapered exterior of the implement collet;
    a guide sleeve for closely receiving the tool implement;
    a guide sleeve collet located inside the front end of the base and having an open end that is adapted to closely receive the guide sleeve the guide sleeve, collet being radially expansible and contractible to selectively retain the guide sleeve;
    a collar located between the linkage and the collet receiver for axially moving the collet receiver in response to rotation of the sleeve; and wherein
    an amount of axial extension of a tool head of the implement from the resecting tool may be selected by a user by axially repositioning the shaft of the implement within the implement collet.

12. The tool of claim 11, further comprising a pair of springs located within the base in engagement with the collet receiver and in axial opposition to each other for counterbalancing the linkage between the locked and unlocked positions of the sleeve.

13. The tool of claim 11 wherein the base has a helical slot and the linkage comprises a locking element carried in the helical slot between the sleeve and the collar, wherein rotation of the sleeve translates the locking element from one end of the slot to the other to axially reposition the collar and, thus, the collet receiver relative to the implement collet.

14. The tool of claim 13 wherein the helical slot comprises a pair of helical slots located opposite of each other in a circumference of the base, and wherein the locking element comprises a ball in each of the helical slots.

15. The tool of claim 11 wherein the collet receiver has an external flange which abuts the collar and acts as a brake against rotation of the implement when the sleeve is in the unlocked position.

16. The tool of claim 11, further comprising:
    a guide sleeve for closely receiving the tool implement;
    a guide sleeve actuation member mounted to a front end of the base and having an external, manually engagable portion, the guide sleeve actuation member being manually movable relative to the base;
    a guide sleeve collet located inside the front end of the base and the guide sleeve actuation member, the guide sleeve collet having an open end that is adapted to closely receive the guide sleeve, the guide sleeve collet being radially expansible and contractible in response to movement of the guide sleeve actuation member relative to the base; and wherein
    an amount of axial extension of the guide sleeve from the resecting tool may be selected by the user, independently of the axial extension of the implement, by axially repositioning the guide sleeve within the guide sleeve collet.

17. The tool of claim 16 wherein the guide sleeve collet is a spring-like metal member having a serpentine cut and an external taper for engaging an internal taper in the guide sleeve actuation member.

18. The tool of claim 16 wherein the guide sleeve actuation mechanism comprises a collet nut that threadingly engages the front end of the base, the collet nut having an internal, circumferentially-extending rib for engaging an annular recess in an exterior of the guide sleeve collet, so that axial movement of the collet nut relative to the base as the collet nut is rotated moves the guide sleeve collet axially.

19. The tool of claim 18 wherein an interior surface of the front end of the base is tapered to couple with a taper on the exterior of the guide sleeve collet, such that axial movement of the guide sleeve collet by the collet nut radially expands and contracts the guide sleeve collet.

20. The tool of claim 11 wherein the collar engages the collet receiver to act as a brake against its rotation when the sleeve is in the unlocked position.

21. A surgical resecting tool for cutting bone that is adapted to be driven by a motor for rotating a tool implement having a shaft and a tool head on one end of the shaft, comprising:

a generally tubular base having a longitudinal axis, a front end with an interior surface that is tapered, and a rear end that is adapted to be attached to the motor;

a drive chuck coaxially mounted in the base and having a first end that is adapted to be coupled to and rotationally driven by the motor and a second end for closely receiving the shaft of the implement;

an implement actuation mechanism mounted to the base and having an external, manually engagable portion that is movable between locked and unlocked positions for moving the second end of the drive chuck into and out of frictional engagement, respectively, with the shaft of the implement;

a guide sleeve for closely receiving the tool implement;

a collet nut rotatably mounted to the front end of the base and having an internal, circumferentially-extending rib;

a guide sleeve collet located inside the front end of the base and the collet nut, the guide sleeve collet having a serpentine cut, an external taper for sliding engagement with the tapered interior surface of the base, an external annular recess for engaging the rib on the collet nut to prevent axial movement therebetween, and an open end for closely receiving the guide sleeve, the guide sleeve collet being radially expansible and contractible along its taper in response to axial movement of the collet nut relative to the base; and wherein an amount of axial extension of a tool head of the implement from the resecting tool may be selected by a user by axially repositioning the shaft of the implement within the second end of the chuck; and wherein an amount of axial extension of the guide sleeve from the resecting tool may be selected by the user, independently of the axial extension of the implement, by axially repositioning the guide sleeve within the guide sleeve collet.

22. The tool of claim 21 wherein the second end of the chuck comprises a collet that is radially expansible and contractible for engaging the shaft of the implement.

23. The tool of claim 21 wherein the implement actuation mechanism comprises:

a sleeve mounted to an exterior of the base for manual rotation relative thereto between the locked and unlocked positions;

a collet receiver having a tapered inner surface, the implement collet having a tapered exterior which is slidingly engaged by the tapered inner surface, and wherein the collet receiver moves axially between the locked and unlocked positions; and a linkage extending between the sleeve and the collet receiver for converting the rotational movement of the sleeve into axial motion of the collet receiver.

24. The tool of claim 23, further comprising a pair of springs located within the base in engagement with the collet receiver in axial opposition to each other for counterbalancing the implement actuation mechanism between the locked and unlocked positions.

25. The tool of claim 23 wherein the base has a helical slot and the linkage comprises a locking element carried in the helical slot in the base between the sleeve and the collet receiver, wherein rotation of the sleeve translates the locking element from one end of the slot to the other to axially reposition the collet receiver relative to the implement collet.

26. The tool of claim 25 wherein the locking element comprises a ball.

27. The tool of claim 21 wherein the implement actuation mechanism engages the drive chuck to act as a brake against its rotation when in the unlocked position.

28. A method for varying the amount of axial extension of a tool implement and a guide sleeve from a surgical resecting tool, comprising:

(a) providing a resecting tool with a mounting end, an opening on an opposite end, a guide sleeve actuation member, an implement actuation mechanism, and an internally rotatable chuck with a motor end and an implement end located opposite the motor end;

(b) attaching the mounting end of the resecting tool to a motor such that the motor end of the chuck couples to and rotationally engages the motor;

(c) moving the guide sleeve actuation member to an open position;

(d) inserting a guide sleeve into the opening in the resecting tool;

(e) selecting a desired length of axial extension of the guide sleeve from the opposite end of the resecting tool by axially moving the guide sleeve relative to the guide sleeve actuation member;

(f) moving the guide sleeve actuation member to a closed position to prevent the guide sleeve from moving relative to the resecting tool;

(g) moving the implement actuation mechanism to an unlocked position;

(h) inserting a shaft of the tool implement into the guide sleeve and the opening in the resecting tool;

(i) selecting a desired length of axial extension of the implement from the opposite end of the resecting tool and the guide sleeve by axially moving the shaft of the implement relative to the implement end of the chuck; and (j) moving the implement actuation mechanism to a locked position to prevent relative axial and rotational motion between the implement and the chuck.

29. The method of claim 28 wherein steps (c) and (f) comprise rotating the guide sleeve actuation member relative to the resecting tool.

30. The method of claim 28 wherein steps (g) and (j) comprise rotating the implement actuation mechanism relative to the resecting tool.

31. The method of claim 28 wherein steps (f) and (j) comprise frictionally engaging the guide sleeve and the implement, respectively.

32. The method of claim 28 wherein the implement actuation mechanism brakes the chuck from rotation when it is in the unlocked position.

33. The method of claim 28 wherein steps (e) and (i) are performed independently of one another.

34. A surgical resecting tool for cutting bone, comprising:

a generally tubular base;

a drive chuck for rotatably driving a tool implement, the drive chuck located within the base for coaxial rotation relative thereto;

a guide sleeve for closely receiving a tool implement; and a guide sleeve collet located inside the front end of the base, the guide sleeve collet having an open end that is adapted to closely receive the guide sleeve and being radially expansible and contractible so that an amount of axial extension of the guide sleeve from the resecting tool may be selected by a user.

35. The tool of claim 34 further comprising a guide sleeve actuation member having an external, manually engagable portion, the guide sleeve actuation member being moveable relative to the base to radially expand and contract the guide sleeve collet.

36. The tool of claim 34 further comprising an implement collet mounted to the chuck for receiving the shaft of a tool implement.

* * * * *